United States Patent [19]

Howard et al.

[11] Patent Number: 5,788,832
[45] Date of Patent: Aug. 4, 1998

[54] TEMPERATURE COMPENSATED ELECTROCHEMICAL GAS SENSOR AND METHOD FOR CLOSELY TRACKING THE TEMPERATURE VARIATIONS OF A GAS TO BE SENSED

[75] Inventors: Charles Peter Howard, Ann Harbor, Mich.; Naim Akmal, Hacienda Heights, Calif.

[73] Assignee: Teledyne Industries, Inc., Los Angeles, Calif.

[21] Appl. No.: 683,985

[22] Filed: Jul. 19, 1996

[51] Int. Cl.⁶ .................................................. G01N 27/404
[52] U.S. Cl. ........................... 205/775; 204/408; 204/415; 205/782.5; 205/783
[58] Field of Search ............................ 204/415, 408; 205/782.5, 783, 775

[56] References Cited

U.S. PATENT DOCUMENTS

| | | | |
|---|---|---|---|
| 3,351,544 | 11/1967 | Medlar | 204/415 |
| 3,767,552 | 10/1973 | Lauer | 204/195 P |
| 4,324,256 | 4/1982 | Vesterager | 204/415 |
| 4,367,133 | 1/1983 | Lauer | 204/195 |
| 4,495,051 | 1/1985 | Fujita et al. | 204/415 |
| 5,085,759 | 2/1992 | Harker | 204/415 |
| 5,425,868 | 6/1995 | Pedersen | 204/415 |

Primary Examiner—T. Tung
Attorney, Agent, or Firm—Edward J. DaRin

[57] ABSTRACT

An electrochemical gas sensor having a temperature sensitive element such as a thermistor arranged within the gas sensor in a temperature insulative fashion for preventing any variations in the temperature of the applied gases to be sensed to be immediately conveyed to the temperature sensitive element thereby providing accurate temperature compensation signals to be combined with the generated sensor electrical output signals. The temperature sensitive element or thermistor is mounted in a heat sink to the expansion membrane of the gas sensor to be responsive only to changes in the temperature variations imparted by the sensor electrolyte and not by the variations in the temperature of the gas sensor body and associated elements thereby providing correct temperature compensation signals without error producing time delays.

8 Claims, 5 Drawing Sheets

TEMPERATURE COMPENSATED ELECTROCHEMICAL GAS SENSOR AND METHOD FOR CLOSELY TRACKING THE TEMPERATURE VARIATIONS OF A GAS TO BE SENSED

FIELD OF THE INVENTION

This invention relates to electrochemical gas sensors for electrically signalling the concentration of an electrochemically active gas, such as oxygen, in a gas mixture and more particularly to improved apparatus and methods for closely tracking temperature variations of the gases applied to the gas sensor permitting accurate compensation for the temperature variations.

BACKGROUND OF THE INVENTION

Electrochemical gas sensors are well known in the prior art for accurately detecting the concentration of an electrochemically active gas, such as oxygen, in a gas mixture. The concentration of the gas is externally signalled by the electrical signal generated by the presence of the active gas that is oxidized or reduced at the surface of the gas sensing cathode electrode. The gas sensors comprise anode and cathode electrodes immersed in a pool of a liquid electrolyte. The electrical output signal from these gas sensors are in the form of an electrical current that corresponds to the partial pressure of the active gas being sensed. The current signal can be converted to a voltage signal by the mounting of a suitable resistor across the output terminals of the gas sensor to derive a voltage signal in millivolts. Covnentionally, a printed circuit board is mounted to the gas sensor at the back side thereof with a suitable resistor thereon for providing the voltage output signal. It is known that the gas sensor output signals are dependent on the temperature of the gas mixture applied thereto. The output signals from the sensors increase with an increase in the temperature of the applied gases. This change in output signal is due to the change in the diffusion rate of the gas mixture through the input membrane for the gas sensor. At the higher temperatures, the electrical output signal increases due to the high diffusion rate of the gases through the input membrane for the gas sensor. As a result, the output signal increase results in an erroneous output signal of the concentration of the gas sensed. To compensate the output signals for the temperature variations and provide accurate output signals, a suitable thermistor is conventionally mounted on the printed circuit board on the rear of the gas sensor. The thermistor provides an electrical output signal for adjusting or compensating the sensor output signal for the temperature variations in the applied gas. This enables the gas sensor to provide accurate measurements of the concentrations of the sensed active gas at various temperatures without any additional correction being required. These gas sensors have a sensing membrane at the front side for receiving the gas mixture to be analyzed. A pool of electrolyte is stored between the input sensing membrane and an expansion membrane. The thermistor is spaced from the electrolyte. This prior art arrangement of the thermistor in gas sensors has been found to take a long time to equilibrate the changes in temperature of the gas mixture applied to the sensor in order to provide a temperature compensation signal. The thermistor in these prior art sensor arrangements is exposed to the gas undergoing analysis immediately upon application of the gas mixture to the sensor, while it takes 30–40 minutes for the sensor body to see a change in the temperature of the applied gas mixture. As a result of this time delay there is an initial low reading due to the adjustment performed by the thermistor. This time delay may be on the order of 30 minutes to one hour. In medical applications wherein it is necessary to monitor the oxygen concentration given to a patient in a critical care unit, this delay may be too long and the error associated with the delayed temperature tracking could be up to 10 per cent of the oxygen required by a patient and could be detrimental to the patient. Accordingly, there is a present need for an improved apparatus and method for more closely tracking and compensating a sensor electrical output signal for errors introduced by varying temperatures of the gas mixtures applied to the gas sensor to be analyzed.

SUMMARY OF THE INVENTION

The present invention is an improved, more sensitive, electrochemical gas sensor having improved methods and means for tracking the temperature changes in the gases applied to the sensors for permitting the temperature compensation signals to be rapidly developed and utilized without any time delay, for providing correct, temperature compensated output signals and thereby accurate electrical output signals representative of the concentrations of the electrochemical active gases applied to the gas sensor to be analyzed. The above advantages are produced with small change in the cost of producing the improved gas sensor.

From a structural standpoint, the improved electrochemical gas sensor includes thermistor means mounted adjacent to an expansion membrane, that is in contact with the gas sensor electrolyte and contains same, in a substantially thermal isolated relationship with respect to the temperature of the gases to be sensed conveyed to the gas sensor so that any change in the temperature of the gas to be sensed is not directly conveyed to the thermistor means whereby the gas sensor and the thermistor means both experience any change in temperature of the gas to be sensed at substantially the same time whereby said thermistor means provides electrical output signals in response to the sensed temperature changes in the gases being sensed without any substantial time delays between the temperature changes in the gases to be sensed and the electrical output signals provided by the thermistor means.

From a broad method standpoint, the present invention comprehends the provision of an electrochemical gas sensor to provide an electrical output signal in response to the application of a gas mixture to the gas sensor having an electochemically active gas to be sensed therein due to the production of a cathodic reaction whereby the electrical output signal is representative of the concentration of the sensed electrochemically active gas that varies with the temperatures of the gas mixtures thereby resulting in erroneous electrical output signals due to the temperature variations of the gas mixture, mounting thermistor means in the gas sensor in a preselected thermal insulative manner for minimizing any direct heat transfer to the thermistor means so that the gas sensor body and the thermistor means are exposed to the temperature variations of the gas mixture at essentially the same time for thereby permitting accurate compensation of the electrical output signals from the gas sensor, without any time delay, thereby providing accurate output signals of the concentrations of the sensed gases despite temperature variations in the applied gas mixtures.

The method includes the steps of mounting the thermistor means in a heat sink adjacent the gas sensor electrolyte and providing a plurality of thermal insulators stacked in the gas sensor with the thermistor means lead wires spiraled into coils and electrically accessible outside the gas sensor.

BRIEF DESCRIPTION OF THE DRAWINGS

These and other features of the present invention may be more fully appreciated when considered in light of the following specification and drawings, in which.

DETAILED DESCRIPTION OF THE PREFERRED EMBODIMENT OF THE INVENTION

Figure 1:
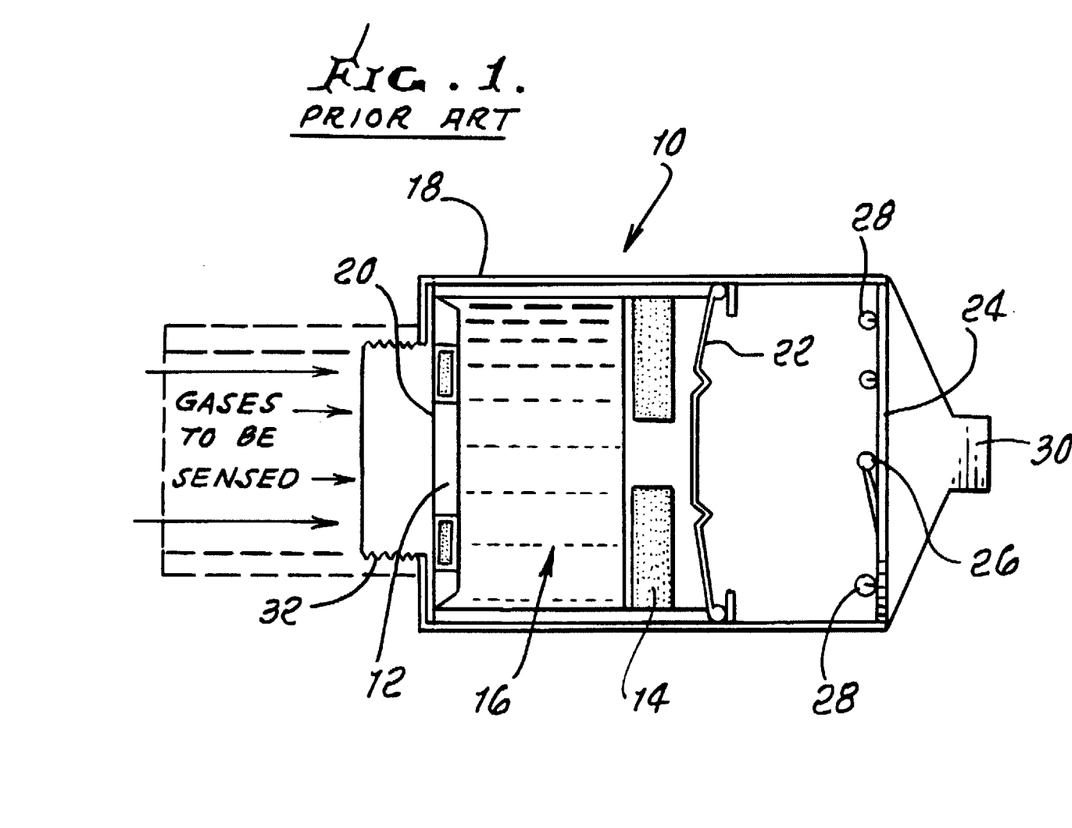
FIG. 1 is cross sectional view of a prior art electrochemical gas senor having thermistor temperature compensation.

An understanding of the problem of the present day organization of electrochemical gas sensors and the temperature compensation of the sensor electrical output signals by means of thermistor means leads to a better appreciation of the need for the improvements disclosed herein and the benefits of the novel structures. The electrochemical gas sensor 10 is illustrated in FIG. 1 as a prior art galvanic type of gas sensor for producing a cathodic reaction at the gas sensing cathode electrode 12 for the gas sensor. The cathodic reaction is produced in response to gas mixtures applied to the gas sensor 10 when the cathode electrode 12 and the associated anode electrode 14 are wet by a suitable electrolyte 16 stored in the container 18 defining the body for the sensor 10. The electrolyte 16 has a preselected volume defined between the thin sensing membrane 20 and the expansion membrane 22 spaced on the opposite side of the anode electrode 14 from the cathode electrode 12. The back side of the container 18 is closed off by the provision of a printed circuit board 24 illustrated spaced from the membrane 22 and mounting a thermistor 26 and a plurality of resistors 28. An electrical connector 30 is connected to the printed circuit board 24 for deriving the electrical output signals produced by the aforementioned cathodic reaction and the thermistor signals to be combined for compensating for any temperature changes in the gas mixture applied to the gas sensor 10 in a well known manner. This structure is typical of the prior art galvanic type of electrochemical gas sensors capable of sensing the concentrations of electrochemically active gases, such as oxygen, in the gas mixtures applied to the gas sensor in parts per million. It should be recognized by those skilled in the art that the present invention is also applicable to other types of gas sensors including polarographic type gas sensors.

As illustrated in FIG. 1, the open end of the container 18 is illustrated with an open ended threaded member 32 for receiving the gas mixtures applied to the gas sensor 10. This permits the gas sensor 10 to be threaded to a suitable-gas block for receiving the gas mixtures flowing through to impinge against the sensing membrane 20. Such a gas block may be constructed of aluminum or plastic. The gas block is diagrammatically illustrated in dotted outline secured to the member 32 in FIG. 1. Upon the application of the gas mixture to be analyzed to the gas sensor 10 the concentration of the electrochemical active gas in the gas mixture produces a cathodic current that is due to the oxidation or reduction of the active gas providing an electrical current output signal from the sensor 10 representative of the concentration of the active gas in the gas mixture. The electrical current can be converted to a voltage output signal by the provision of a suitable output resistor coupled across the output terminals of the sensor 10. A ten ohm resistor mounted on the printed circuit board 24, for example will convert the output currents to a voltage signal in millivolts. It is also well known that electrical output signals from the gas sensors 10 are also dependent on the temperature and the temperature variations of the gas mixtures applied to the sensor. The electrical output signals increase in magnitude with the increases in the temperatures of the gas mixture being sensed or analyzed. This change in output signal is due to the change in the diffusion rate of the applied gas through the thin sensing membrane 20. At the higher gas temperatures the output electrical signals increase due to the high diffusion rate of the applied gas through the sensing membrane 20 and thereby the derived output signals erroneously signal the concentration of the sensed active gas in the applied gas mixture. The prior art gas sensors utilized a temperature sensing device in the form of the thermistor 26 mounted on the printed circuit board 24 for the gas sensor 10 to provide an electrical output signal representative of the temperature change in the applied gas to the gas sensor. The thermistor output signal is utilized as a temperature compensating signal for the erroneously generated sensor output signal to provide the correct output signal compensated for the temperature variations, as well known, without the need for additional corrections. The thermistor signals are utilized to cancel out the temperature components of the sensor generated signals in a known circuit manner. As can be appreciated from viewing FIG. 1, the gas mixture to be analyzed is immediately exposed to the thermistor 26 and as a result signals a temperature change that produces an initial low, erroneous output signal from the gas sensor 10. It is known that the gas sensor body takes a time period on the order of 30–40 minutes to change in temperature before it will correctly signal the temperature change in the applied gas mixture. This time delay in providing accurate electrical output signals has been found to be between 30 minutes to one hour. For a patient in a critical care unit wherein the supply of oxygen, for example, is monitored this time delay is excessive and the errors introduced with the delayed temperature tracking by the thermistor could be up to 10% of the required oxygen supply and could be detrimental to a patient.

Figure 2:
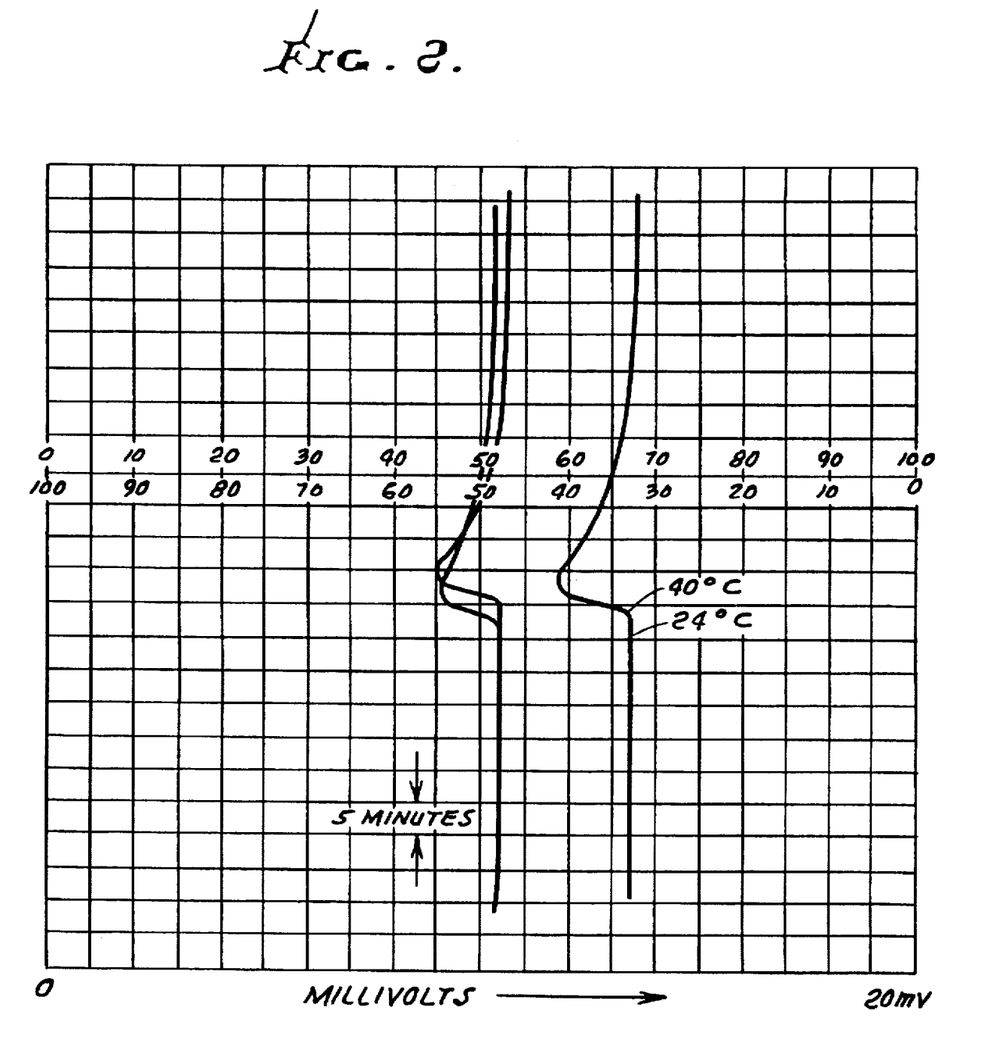
FIG. 2 is a graphical illustration of the gas sensor of FIG. 1 electrical output signal variations due to increased temperatures of the gas mixture applied to the gas sensor.

The time delay introduced by the erroneous temperature tracking by the thermistor 26 for the gas sensor 10 is graphically illustrated in FIG. 2 for a temperature change from 24 degrees centigrade to 40 degrees centrigade for tests conducted on three different gas sensors of the type of gas sensor 10. The space between the vertical lines in FIG. 2 represent 5 minutes in time. All three gas sensors signalled an immediate drop in the value of the electrical output signal due to the thermistor 26 being immediately exposed to the temperature change with a gradual increase in value as the sensor body absorbs the temperature change with time. The electrical output signal reaches a steady state condition after the time delay period required by the sensor body and associated elements to reach the changed temperature, in the above example the 40 degrees C. This time delay period for the cells of FIG. 2 can be seen to be substantial, on the order of 30 minutes.

Figure 3:
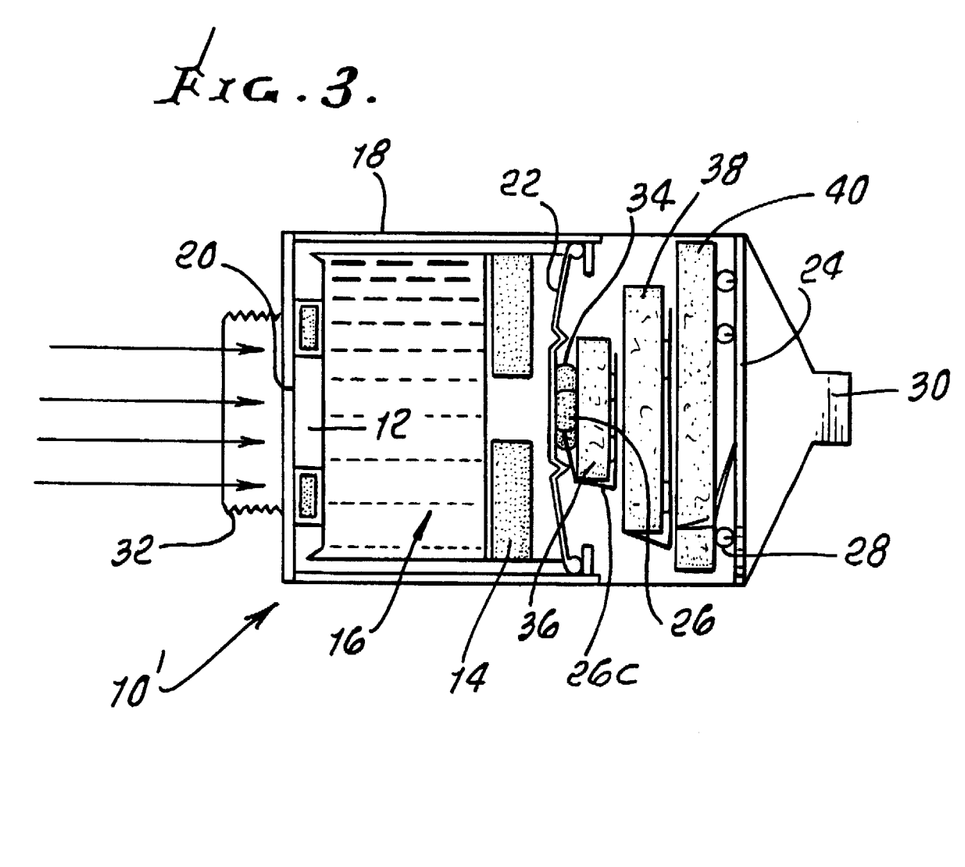
FIG. 3 is a cross sectional view of an electrochemical gas sensor having means for closely tracking temperature variations of the gas mixtures applied to the gas sensor and embodying the present invention.
Figure 5:
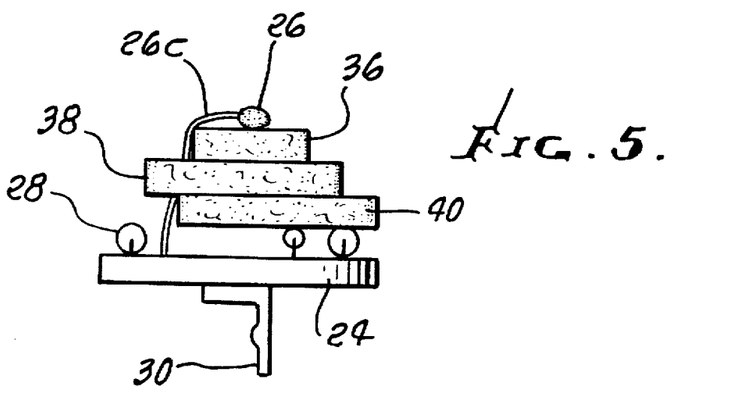
FIG. 5 is a side view of the thermistor arrangement as viewed in FIG. 4.
Figure 6:
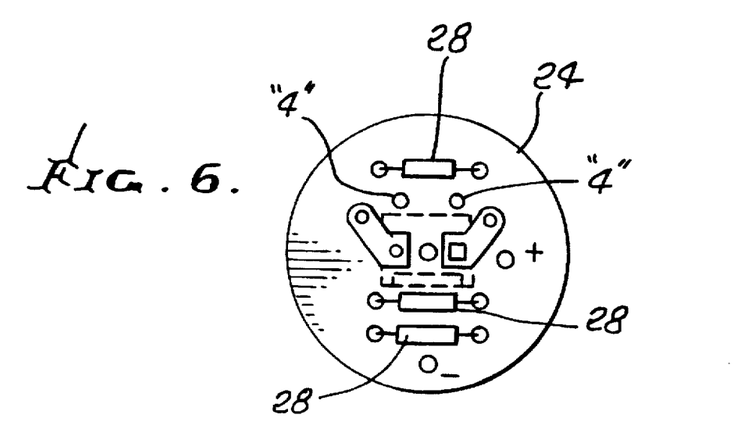
FIG. 6 is a detached view of the top of the printed circuit board assembly as utilized in the gas sensor of FIG. 3.
Figure 7:
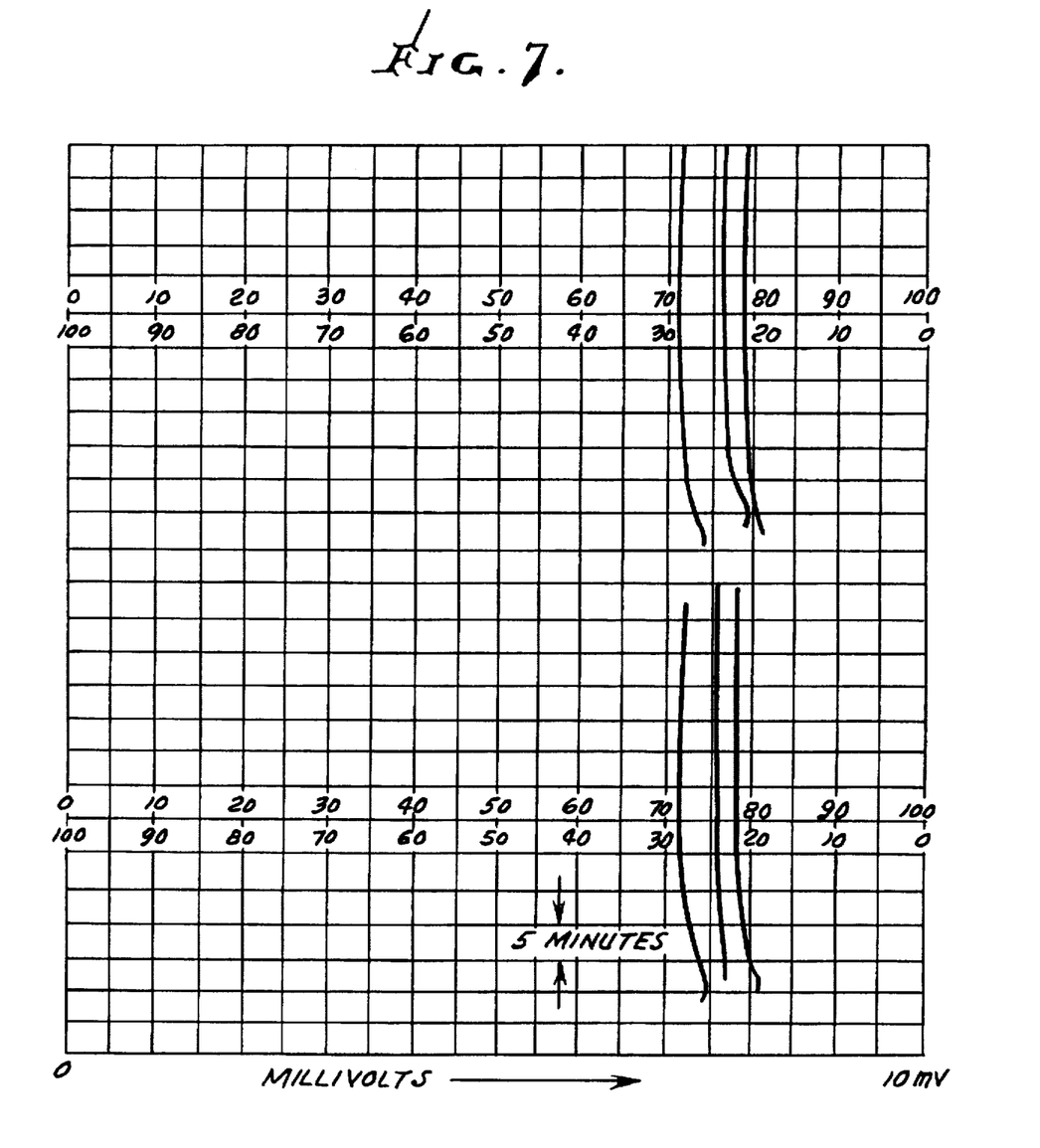
FIG. 7 is a graphical illustration of the gas sensor of FIGS. 3–6 electrical output signal variations due to the increase in the temperature of the gas mixture applied to the gas sensor.

With the above prior art structures and problems in mind, the improved gas sensor 10' of the present invention will be examined in conjunction with the structures illustrated in FIGS. 3–6 and the graphical representation of FIG. 7. The basic structure of the galvanic type electrochemical gas sensor 10 of FIG. 1 is illustrated in FIG. 3 but illustrating the improved arrangement for sensing the applied gas temperatures and tracking the temperatures without introducing the time delays of the prior art structures. The thermistor 26 in accordance with the present invention is located in very close proximity to the liquid electrolyte adjacent the expansion membrane 22 and in a substantially thermally insulated relationship with the gas sensor body and the gases applied to the gas sensor 10' and is responsive to the temperature changes imparted to the electrolyte and thereby eliminates the prior art time delays involved in tracking the temperatures of the gases applied to the gas sensors during a change in the temperature of the gases.

To this end, the thermistor 26 is potted to the rear side of the expansion membrane 22 with a heat sink compound 34, such as a zinc oxide or silicone, as illustrated in FIG. 3. In this manner, any change in temperature of the gases undergoing analysis are not directly conveyed to the thermistor 26 to produce erroneous signal outputs. The lead wires for the thermistor 26 comprise an electrically insulated cable 26C of approximately 3–4 inches in length having the individual lead wires thereof secured to the printed circuit board 24 at the points "4" on the board; see FIGS. 4 and 6.

Figure 4:
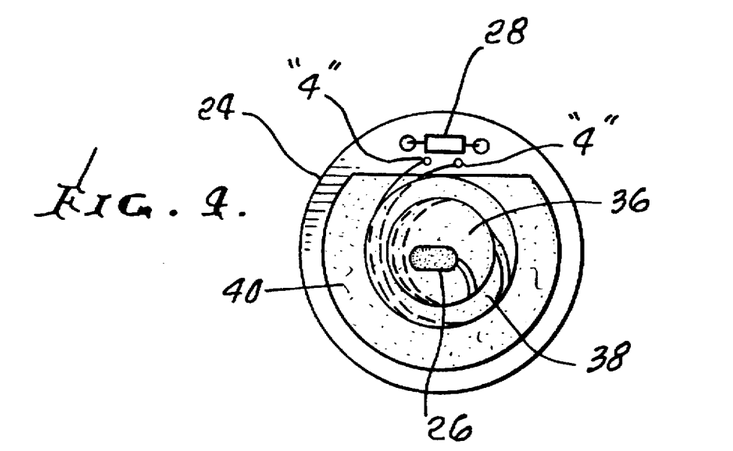
FIG. 4 is a view from the top of an unpatted, thermistor, looking towards the back side of the gas sensor of FIG. 3 and illustrating the spiral assembly of the thermistor leads, in part illustrated in dotted outline.

Another important feature of the assembly of the thermistor 26 to the gas sensor 10' is the provision of thermal insulative means arranged between the heat sink compound 34 and the tops of the circuit board devices on the printed circuit board 24 as best illustrated in FIGS. 3 and 5. The insulative means, as illustrated, comprises three individual layers of foam stacked upon one another between the heat sink 34 and the printed circuit board 24. The individual layers of foam insulation are each a different size and are identified in the drawings as layers 36, 38 and 40 from the top to the bottom, see FIG. 5, in particular. The top most insulative layer 36 is positioned below the thermistor 26 and the heat sink compound 34 and is the smallest in size, diameter wise, of the three insulative layers. The bottom insulative layer 40 is the largest in diameter while the layer 38 is intermediate in size between the diameters of layers 36 and 40. The thickness of the three layers are essentially the same and in combination occupy the volume between the heat sink compound 34 and the printed circuit board 24. The three layers are arranged in a staggered relationship as best seen in FIG. 5. The insulative cable 26C for the thermistor 26 is spiraled or coiled between the insulative layers 36, 38 and 40 between the stacked layers, see FIGS. 3 and 4, and the individual lead wires of the cable 26C are connected to point "4" on the printed circuit board 24, as best seen in FIGS. 4 and 6.

In the above described manner of insulatively securing the thermistor 26 any change in temperature of the gas mixtures applied to the gas sensor 10' is not directly conveyed to the thermistor 26 since the gas sensor container or body 18 and the thermistor both experience the change in gas temperature at essentially the same time. Therefore, the electrical output signals developed by the gas sensor 10' and the thermistor 26 when combined, correctly compensates the sensor generated electrical output signals for the sensed temperature variations so that the resulting temperature compensated electrical output signals are true representations of the signals produced at the gas sensing cathode electrode, without any erroneous increases or decreases due to temperature changes.

The gas sensor 10' was tested in the identical manner as the sensor 10 and plotted in FIG. 7 for a temperature change in the sensor applied gas from 24 degrees C. to 40 degrees C. In FIG. 7, the output signals for six gas sensors are illustrated as coming to equilibrium right away, without any false increasers or decreases in electrical output signals as in the known prior art devices.

It should now be appreciated by those skilled in the gas sensor art that the present disclosure has advanced the art: for precisely tracking the temperature changes in the gas mixtures applied to the gas sensor so as to provide more sensitive and accurately compensated electrical output signals that better track temperature changes. This tracking results due to the thermistor being responsive to the temperature changes imparted to the liquid electrolyte and not the temperature changes of the sensor body.

We claim:

1. An electrochemical gas sensor for sensing the concentration of an electochemically active gas, such as oxygen, in a gas mixture to be analyzed and providing sensor electrical output signals representative of the sensed concentrations, said gas sensor comprising an insulative sensor container having an open end and adapted for storing a liquid electrolyte in the container, means for defining a gas sensing cathode electrode supported within the container adjacent said open end of the insulative sensor container, a gas permeable, liquid impermeable membrane secured to said open end of said container in intimate contact with the cathode electrode and having a preselected thin thickness for limiting the diffusion of the gases to be sensed and to be conveyed to said cathode, an expansion membrane mounted within said sensor container and being spaced a preselected distance from said open end and for storing an electrolyte in the volume between said gas permeable membrane and the expansion membrane, a liquid electrolyte stored in the volume between said gas permeable membrane and the expansion membrane, means for defining an anode electrode mounted in the electrolyte adjacent the expansion membrane, the improvement comprising thermistor means mounted on the expansion membrane in a substantially thermal isolated relationship with respect to the temperature of the gases to be sensed that are conveyed to said gas permeable membrane so that any change in the temperature of the gas to be sensed is not directly conveyed to the thermistor means except by means of the temperature changes imparted to the electrolyte whereby the sensor and the thermistor means both experience any change in temperature of the gas to be sensed at substantially the same time whereby said thermistor provides electrical output signals in response to the sensed temperature changes without any substantial time delays between the temperature changes and the thermistor electrical output signals useful for temperature compensation of said sensor electrical output signals.

2. An electrochemical gas sensor as defined in claim 1 wherein said thermistor means is secured to said expansion membrane with a thermal insulator so as to be substantially sensitive only to temperature changes of said electrolyte for providing temperature compensation signals for the output signals generated by said gas sensor.

3. An electrochemical gas sensor as defined in claim 2 wherein said thermistor means is secured to said expansion membrane with heat sink means and further including a printed circuit board for enclosing the end of said insulative container opposite to said open end thereof, a plurality of thermal insulators stacked between said thermistor means and said printed circuit board for minimizing any direct heat transfer from said gases to be sensed to the thermistor means, said thermistor means having an insulated electrical cable spiraled between said stacked thermal insulators and connected to said circuit board.

4. An electrochemical gas sensor as defined in claim 3 wherein said plurality of thermal insulators comprise individual insulators of different sizes that increase in size from adjacent said thermistor means to said printed circuit board.

5. An electrochemical gas sensor as defined in claim 3 wherein said plurality of thermal insulatots comprise three thermal insulators stacked between said thermistor means and the printed circuit board, the thermal insulator adjacent said thermistor means being the smallest insulator and the largest insulator being adjacent said circuit board, and the third insulator being of a size larger than the smallest insulator and smaller than the largest insulator and stacked intermediate the small and large insulators, said insulated thermistor having lead wires spiraled into coils of increasing diameter between the smallest and the third insulators and between the largest and the third insulators and being electrically connected to said circuit board.

6. A method of compensating an electrochemical gas sensor for sensing the concentration of an electrochemically active gas in a gas mixture applied to the sensor for temperature changes in said gas mixture, the gas sensor providing electrical output signals representative of the sensed electrochemically active gas that vary with the temperature variations of the applied gas mixture, the method includes the steps of providing an electrochemical gas sensor having an insulative container having a gas sensing cathode electrode and an anode electrode mounted in the container with an electrolyte, said container having an open end adjacent the cathode electrode for applying the gas mixture to the cathode electrode and an expansion membrane mounted to said container in a preselected spaced relationship with said open end of the container and containing the electrolyte, mounting thermistor means on the expansion membrane to be responsive to temperature changes of said applied gas mixture imparted to the electrolyte, securing the thermistor means to the expansion membrane with heat sink means so as to substantially prevent any temperature changes of said applied gas mixture from being directly transmitted to the thermistor means so that said gas sensor and the thermistor means both respond to any temperature changes at substantially the same time, mounting thermal insulative means on the opposite side of the thermistor means from the side secured to the expansion membrane, the thermistor means including insulated lead wires extending therefrom for deriving temperature compensating electrical signals from said gas sensor, and arranging said leads with said thermal insulative means so as to be contained within said insulative means to prevent temperature changes of said applied gas mixture to be conducted to said thermistor means and permitting said leads to be accessible ouside of the gas sensor.

7. A method of compensating an electrochemical gas sensor as defined in claim 6 wherein the step of mounting thermal insulative means includes the steps of stacking a plurality of thermal insulative means, each of a different, preselected size, for thermally insulating the thermistor means, and spiralling said lead wires of the thermistor means in an insulative relationship between each of the stacked, plurality of insulative means and arranged to be accessible externally of the gas sensor.

8. A method of compensating an electrochemical gas sensor as defined in claim 7 wherein the step of spiralling the lead wires comprises wrapping the lead wires in a coiled configuration between the stacked insulative means.

* * * * *

UNITED STATES PATENT AND TRADEMARK OFFICE
CERTIFICATE OF CORRECTION

PATENT NO. : 5,788,832

DATED : 8/4/98

INVENTOR(S) : Howard et al.

It is certified that error appears in the above-identified patent and that said Letters Patent is hereby corrected as shown below:

Column 7, line 21, delete "insulatots" and substitute --insulators--.

Signed and Sealed this

Twenty-third Day of February, 1999

Attest:

Q. TODD DICKINSON

*Attesting Officer*  *Acting Commissioner of Patents and Trademarks*